United States Patent [19]

Keenan et al.

[11] Patent Number: 5,166,513
[45] Date of Patent: Nov. 24, 1992

[54] DUAL ACTUATION PHOTOELECTRIC FOOT SWITCH

[75] Inventors: Peter B. Keenan, Los Altos; Dave Youngquist, San Jose, both of Calif.

[73] Assignee: Coherent, Inc., Palo Alto, Calif.

[21] Appl. No.: 695,944

[22] Filed: May 6, 1991

[51] Int. Cl.⁵ .............................................. G01V 9/04
[52] U.S. Cl. .................................... 250/221; 200/86.5
[58] Field of Search ............... 250/221, 229; 200/61.7, 200/86.5, 5 A, 18; 340/555, 556, 557; 361/189

[56] References Cited

U.S. PATENT DOCUMENTS

| | | | |
|---|---|---|---|
| 3,805,085 | 4/1974 | Andrews | 250/221 |
| 3,867,591 | 2/1975 | Nordeen | 200/61.7 |
| 4,496,811 | 1/1985 | Irwin | 200/86.5 |
| 4,939,358 | 7/1990 | Herman et al. | 250/229 |

Primary Examiner—David C. Nelms
Assistant Examiner—K. Shami
Attorney, Agent, or Firm—Limbach & Limbach

[57] ABSTRACT

A dual actuation foot switch particularly suited to medical laser systems is disclosed. The foot switch includes a housing having an opening for receiving a foot. A first switch is provided which is actuated by the placement of the foot into the housing. A second switch is actuated by pressure from the user's foot. The dual actuation feature can be used to initiate two different responses from the medical laser system.

14 Claims, 2 Drawing Sheets

DUAL ACTUATION PHOTOELECTRIC FOOT SWITCH

TECHNICAL FIELD

A foot switch is disclosed having two independent actuation mechanisms. The subject foot switch is particularly useful in conjunction with certain medical lasers.

BACKGROUND OF THE INVENTION

A large variety of switches that are operated by a user's foot are found in the prior art. Such switches are desirable when the user's hands are otherwise occupied. For example, foot switches are often used to trigger the delivery of laser energy in a medical laser system. Typically, the doctor will be using his hands to position the patient and the laser delivery system in the proper location. At the desired moment, the doctor will press down on the pedal of the foot switch to deliver the laser energy to the treatment site.

One type of prior art medical laser is described in copending application Ser. No. 654,834, filed Feb. 13, 1991 and incorporated herein by reference. The laser described in the latter application is a solid state, flash lamp pumped, Holmium:YAG laser. This laser is marketed by the assignee under the trademark TwoPointOne.

In operating the TwoPointOne laser at higher pulsed powers, it was found that during the first pulses of the flashlamp, instabilities in the thermal parameters of the rod-shaped gain medium led to deterioration of optical elements in the laser. As described in the latter application, the problem was overcome by preconditioning the laser rod to avoid the instabilities. The rod is preconditioned by initially operating the flashlamp at a energy below the threshold for laser oscillation. In this manner, the rod is allowed to come to thermal equilibrium prior to the generation of the laser beam.

The laser described above is typically actuated by a foot switch. At present, when the doctor presses on the foot switch, the laser will first enter the preconditioning mode during which time the rod is brought into thermal equilibrium. This process takes about one second. As soon as the rod has been preconditioned, the energy to the flashlamp is automatically increased above threshold and a laser beam is generated and delivered.

While this approach has improved the stability and lifetime of the system, a delay has been created between the actuation of the foot switch and the delivery of the laser energy. From the standpoint of the doctor, it would be desirable to eliminate that delay. The subject foot switch has been developed to overcome this problem.

The subject foot switch can be used in other medical laser systems. For example, the assignee herein manufactures and sells a line of ophthalmic medical lasers including the Novus 2000. This system includes a slit lamp through which the ophthalmologist looks to examine the eye of the patient. When the doctor begins to treat the eye with the laser beam, an eye safety filter is dropped into place within the slit lamp to protect the doctor's eye from reflected laser radiation. The safety filter is typically a coated optical element that allows a certain fraction of visible light to pass but substantially blocks radiation at the wavelength of the treatment laser beam.

Because of the reduced transmission of the filter, it is important that the filter be outside of the visual path of the slit lamp while the doctor is examining the patient's eye and aligning the aiming beam of the system just prior to treatment. However, the eye safety filter must be moved into place prior to delivery of the treatment beam. The movement of this filter is not silent and is typically accompanied by a clicking sound immediately followed by a pulse of laser energy. Thus, the patient hears the click made by the movement of the filter and then is hit with the laser beam which causes a certain degree of pain. It has been found that in a short time, the patient will begin to flinch upon hearing the clicking sound of the safety filter moving into place. When the patient flinches, the ability to accurately deliver the treatment beam is diminished.

As can be appreciated, it would be desirable to disassociate the sound of the filter being moved into place from the delivery of the treatment beam. The dual actuation foot switch of the subject invention addresses that need.

Accordingly, it is an object of the subject invention to provide a new and improved dual actuation foot switch.

It is a further object of the subject invention to provide a dual actuation foot switch for use with medical laser systems.

It is still another object of the subject invention to provide a foot switch that can independently initiate the warm-up stage of a laser and subsequently initiate the generation of laser energy.

It is still a further object of the subject invention to provide a foot switch that can independently actuate the movement of a safety filter and subsequently initiate the delivery of laser energy.

SUMMARY OF THE INVENTION

In accordance with these and other objects, the subject foot switch includes a housing having an opening for receiving the foot of the user. A first switch is provided which is actuated by the placement of the foot into the housing. A second, conventional pedal switch is provided for actuating the laser beam.

The first switch can include a hinged door panel which is displaced by the placement of the foot into the housing. In the alternative, the first switch can be defined by light emitter and photocell detector combination. The latter combination can sense when a foot enters the housing.

The first switch functions to generate a first control signal which is transmitted to the laser system. In one embodiment, the control signal is used to initiate the warm-up period of the laser. In an alternate embodiment, the control signal is used to cause the eye safety filter to drop into place. In both cases, the second switch generates a control signal that is used to generate and deliver the laser energy to the treatment site.

Further objects and advantages will become apparent from the following detailed description taken in conjunction with the drawings in which:

DETAILED DESCRIPTION OF THE PREFERRED EMBODIMENTS

Figures 1, 2, 3:
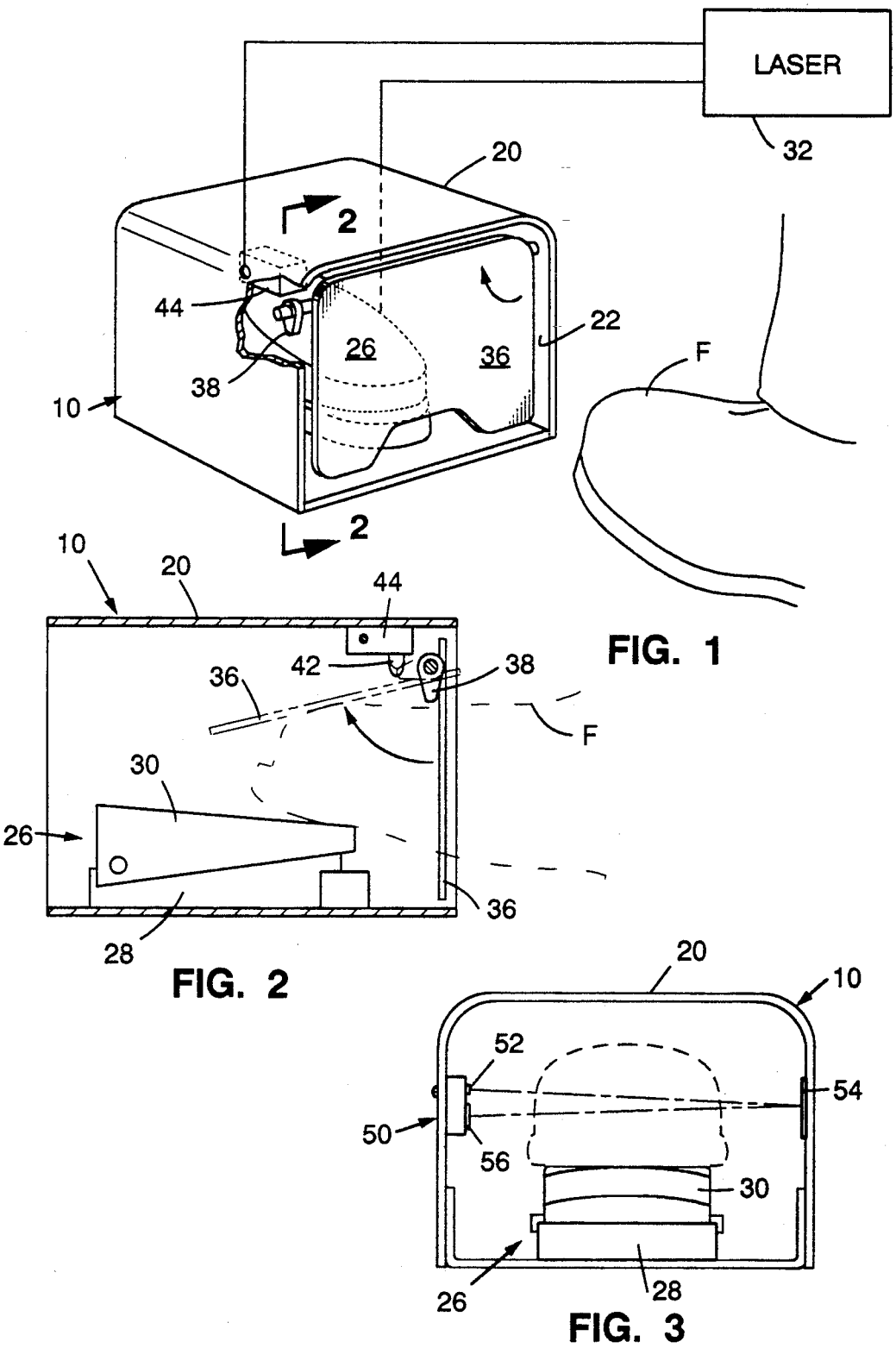
FIG. 1 is a perspective view of the dual actuation foot switch of the subject invention coupled to a laser.
FIG. 2 is a cross sectional view of the subject foot switch taken along the line 2—2 in FIG. 1.
FIG. 3 is an end view of an alternate embodiment of a foot switch formed in accordance with the subject invention.

Referring to FIGS. 1 and 2, the first embodiment of the foot switch 10 of the subject invention is illustrated. The foot switch includes a metal housing 20 which can be substantially rectangular in configuration. The housing includes an opening 22 for receiving the foot F of the user.

A standard foot pedal switch 26 is mounted within and at the bottom of the housing 20. Pedal switch 26 includes a base 28 and spring biased actuator 30. A suitable pedal switch can be obtained from Linemaster Switch Co. of Woodstock, Conn., Clipper Cat. No. 635-S. When the actuator is depressed, a contact will be closed so that a control signal can be generated and transmitted to the laser 32. The housing and foot pedal switch described above have been sold with the assignee's medical laser systems for some time.

In accordance with the subject invention, the foot switch 10 is provided with a second switch mechanism which is actuated by the placement of the user's foot F into the housing. In the first embodiment of the subject invention, the second switch includes a door panel 36 which is hingedly connected to the housing. Door panel 36 is configured cover at least a portion of opening 22. As can be seen in FIG. 2, when a foot F is placed into the housing, door panel 36 will be displaced upwardly.

The displacement of door panel 36 can be used to actuate a trigger mechanism in any suitable fashion. In the illustrated embodiment, door panel 36 carries a cam member 38 which is driven into the contact 42 of a switch 44. When the contact of the switch is closed, a control signal can be generated and supplied to laser 32.

FIG. 3 illustrates an alternate approach for detecting the placement of a foot F into the housing 20. In this embodiment, the second switch is defined by a light emitting diode and photodetector package 50. The LED 52 generates a light output which is directed across the opening 22 of the housing. Preferably, some form of reflector 54 is mounted on the opposed side of the housing. Light bouncing off the reflector is detected by the photocell 56 of the package 50. A suitable package 50 is manufactured by Allan Bradley, Photoswitch No. 880L-RL2.

In operation, when the user's foot is placed in the housing, the path of the light beam is blocked. The decrease in transmitted and reflected power will be evidenced by a drop in the voltage generated by the photocell 56. This drop can be used to generate a control signal that is supplied to laser 32.

Figure 4:
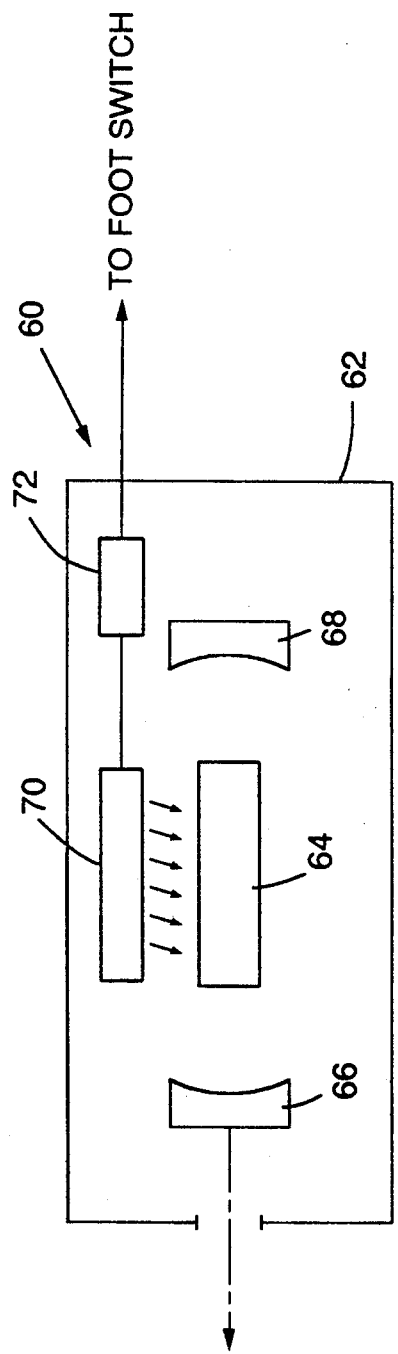
FIG. 4 is a schematic diagram of one type of laser which could be used in conjunction with the subject foot switch.

As noted above, the subject foot switch can be advantageously used with a number of medical laser systems. One such system 60 is illustrated schematically in FIG. 4 and discussed in greater detail in the above cited copending patent application. The laser system 60, marketed under the trademark TwoPointOne, includes a housing 62 within which is mounted a solid state gain medium 64. Solid state gain medium 64 is defined by a Holmium:YAG rod. The rod is located between two mirrors 66 and 68 which define the resonator. The rod is excited by a flashlamp 70. The flashlamp is energized by a power supply 72. The power supply and control circuits are connected to the output of the foot switch 10.

As described above, in the operation of laser system 60, the rod is initially preconditioned to achieve thermal equilibrium prior to generating the laser output. When the laser is first triggered, the flashlamp is energized to a level sufficient to heat the rod but below the laser oscillation threshold. After a short time period, the energy to the flashlamp is increased so that laser light can be generated.

In accordance with the subject invention, the preconditioning cycle can be triggered based on the output of the switch which detects the placement of the foot in the housing. As can be appreciated, this event will always precede the actuation of the foot pedal 26 that initiates the subsequent generation of the treatment beam. By the time the foot pedal switch is actuated, a portion, if not all of the preconditioning cycle will have been completed. Thus, the delay between the actuation of the foot pedal 26 and the delivery of the treatment pulse will be reduced or eliminated.

It is expected that in practice, the doctor's foot will be placed into the housing at a time sufficiently prior to the actuation of the foot pedal 26 so that the preconditioning cycle can be actuated and completed and therefore the generation and delivery of laser light will be essentially simultaneous with the actuation of the foot pedal 26.

Figure 5:
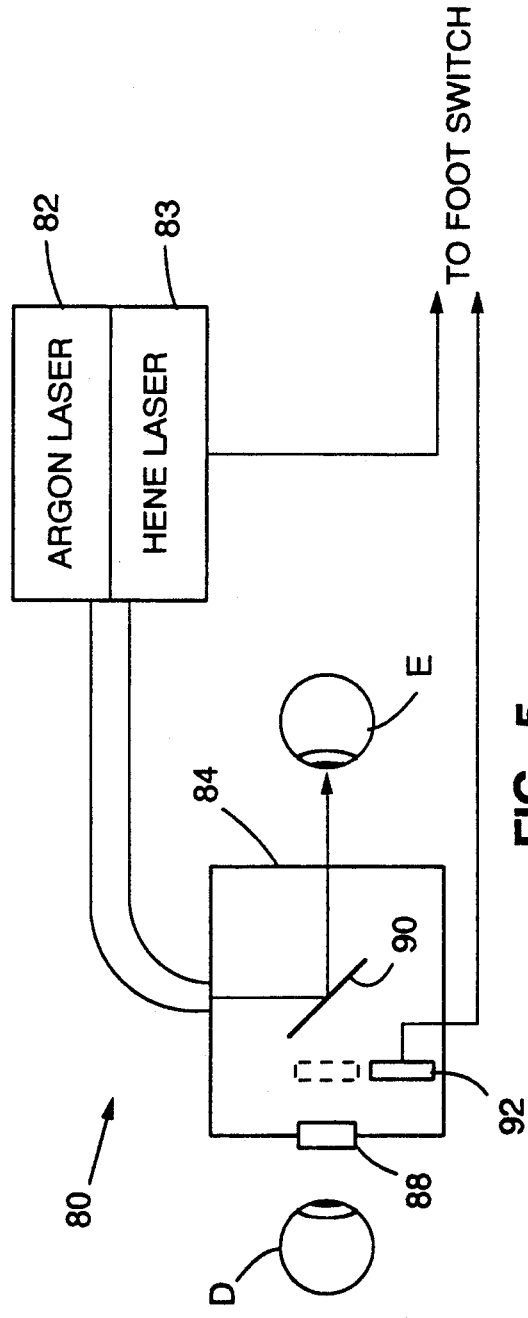
FIG. 5 is a schematic diagram of another type of laser which could be used with the subject foot switch.

FIG. 5 is a schematic illustration of another laser system 80 which can benefit from the subject foot switch. This laser system is marketed by the assignee herein under the trademark Novus 2000. Laser system 80 includes an argon laser 82 for generating a treatment beam. A Helium-Neon laser 83 is used to generate a lower power aiming beam. Both beams are channeled in a collinear manner to a slit lamp 84. A slit lamp is a standard ophthalmic device for examining the eye E of a patient. The slit lamp includes a microscope element 88 through which the doctor D will view the eye E of the patient.

The standard slit lamp is modified when used in conjunction with a laser surgical system. Laser light is deflected into the eye E of the patient by a dichroic filter 90. Visible light for the examination will pass through the filter 90. When the laser light is being delivered, an eye safety filter 92 is moved into the visual path between the doctor and the patient. The eye safety filter is designed to prevent any reflections of laser energy from reaching the doctor. As noted above, it is desirable to locate the eye safety filter out of the field of view of the doctor until treatment begins. It is also desirable to decouple the movement of the filter from the initiation of the laser pulse.

These objects are achieved using the foot switch 10 of the subject invention. More specifically, the doctor can examine the patient and direct the aiming beam to the treatment site with the eye safety filter 92 in the inactive position as shown in solid line in FIG. 5. The doctor can then place his foot into the housing 20. The actuation of the switch which detects the placement of the foot into the housing can then be used to initiate the movement of the eye safety filter into place (as shown in phantom line in FIG. 5). When the doctor sees that the patient has not moved or has returned to his initial position, he can press down on pedal 26 causing the argon treatment beam to be delivered to the treatment site.

As can appreciated, the use of the subject foot switch allows the doctor to independently actuate the eye safety filter and then initiate the delivery of the treatment beam. By this arrangement, the patient will be less likely to flinch when he hears the sound of the eye safety filter moving into place.

In summary there has been disclosed a dual actuation foot switch particularly suited to medical laser systems. The foot switch includes a housing having an opening for receiving a foot. A first switch is provided which is actuated by the placement of the foot into the housing. A second switch is actuated by pressure from the user's foot. The dual actuation feature can be used to initiate two different responses from the medical laser system.

While the subject invention has been described with reference to the preferred embodiments, various changes and modifications could be made therein, by one skilled in the art, without varying from the scope and spirit of the subject invention as defined by the appended claims.

We claim:

1. A foot switch comprising:
   a housing having an opening through which the foot of the user is passed;
   a first switch means actuated by the placement of the foot into the housing through the opening; and
   a second switch means actuated by pressure from the user's foot after the foot has been placed in the housing.

2. A foot switch as recited in claim 1 wherein said first switch means includes a door panel hingedly attached to the housing, said door panel covering at least a portion of said opening, said door panel being displaced inwardly when a foot is placed in the housing.

3. A foot switch as recited in claim 2 wherein said first switch means includes a contact means which is moved from a first position to a second position when engaged by the displaced door panel.

4. A foot switch as recited in claim 1 wherein said first switch means includes means for generating a beam of light extending across the opening, said switch means further including a means for detecting a change in the power of the beam transmitted across the opening, said change induced when a foot is placed into the housing.

5. A foot switch for use with a medical laser, said laser requiring a warm-up stage prior to generation of a treatment beam, said foot switch comprising:
   a housing having an opening through which the foot of the user is passed;
   a first switch means actuated by the placement of the foot into the housing through the opening, said first switch means generating a first control signal for initiating the warmup stage of the laser; and
   a second switch means actuated by pressure from the user's foot after the foot has been placed in the housing, said second switch means generating a second control signal for initiating the delivery of the treatment beam.

6. A foot switch as recited in claim 5 wherein said first switch means includes a door panel hingedly attached to the housing, said door panel covering at least a portion of said opening, said door panel being displaced inwardly when a foot is placed in the housing.

7. A foot switch as recited in claim 6 wherein said first switch means includes a contact means which is moved from a first position to a second position when engaged by the displaced door panel.

8. A foot switch as recited in claim 5 wherein said first switch means includes means for generating a beam of light extending across the opening, said switch means further including a means for detecting a change in the power of the beam transmitted across the opening, said change induced when a foot is placed into the housing.

9. A foot switch for use with a medical laser, said laser having a safety filter the position of which must be changed prior to the generation of a treatment beam, said foot switch comprising:
   a housing having an opening through which the foot of the user is passed;
   a first switch means actuated by the placement of the foot into the housing through the opening, said first switch means generating a first control signal for changing the position of the safety filter; and
   a second switch means actuated by pressure from the user's foot after the foot has been placed in the housing, said second switch means generating a second control signal for generating the treatment beam.

10. A foot switch as recited in claim 9 wherein said first switch means includes a door panel hingedly attached to the housing, said door panel covering at least a portion of said opening, said door panel being displaced inwardly when a foot is placed in the housing.

11. A foot switch as recited in claim 10 wherein said first switch means includes a contact means which is moved from a first position to a second position when engaged by the displaced door panel.

12. A foot switch as recited in claim 9 wherein said first switch means includes means for generating a beam of light extending across the opening, said switch means further including a means for detecting a change in the power of the beam transmitted across the opening, said change induced when a foot is placed into the housing.

13. A laser delivery system including:
   means for delivering a laser treatment beam;
   an eye safety filter; and
   a dual actuation foot switch comprising:
     a housing having an opening through which the foot of a user is passed:
     first switch means within said housing for moving said eye safety filter to a position between said user of said system and a subject being treated; and
     second switch means within said housing for actuating said means for delivering said laser treatment beam, after operation of said first switch means, by the placement of said user's foot on said second switch means;
   wherein said second switch means is not accessible unless said first switch means is being operated.

14. A laser delivery system including:
   a laser rod;
   a flashlamp for exciting said rod; and
   a dual actuation foot switch comprising;
     a housing having an opening through which the foot of a user is passed:
     first switch means within said housing actuated by the placement of said foot into the housing through said opening, said first switch means generating a first control signal for initiating the operation of the laser; and
     second switch means within said housing actuated by the placement of said user's foot on said second switch means, said second switch means generating a second control signal for initiating the delivery of a treatment beam;
   wherein said second switch means is not accessible unless said first switch means is being actuated.

* * * * *